United States Patent [19]

Welborn, Jr. et al.

[11] Patent Number: 4,665,208
[45] Date of Patent: May 12, 1987

[54] PROCESS FOR THE PREPARATION OF ALUMOXANES

[75] Inventors: Howard C. Welborn, Jr., Houston, Tex.; Erik G. M. Tornqvist, Watchung, N.J.

[73] Assignee: Exxon Chemical Patents Inc., Linden, N.J.

[21] Appl. No.: 754,379

[22] Filed: Jul. 11, 1985

[51] Int. Cl.$^4$ ................................................. C07F 5/06
[52] U.S. Cl. ...................................... 556/179; 556/175; 556/187; 502/117; 526/124
[58] Field of Search ................. 556/179, 175, 187

[56] References Cited

U.S. PATENT DOCUMENTS

| | | | |
|---|---|---|---|
| 3,242,099 | 3/1966 | Manyik et al. | 252/429 |
| 3,454,615 | 7/1969 | Tani et al. | 556/179 |
| 4,544,762 | 10/1985 | Kaminsky et al. | 556/179 |

FOREIGN PATENT DOCUMENTS 20861 10/1983 Australia .
0035242 9/1981 European Pat. Off. .

OTHER PUBLICATIONS

*CIS-1,4-Polybutadiene by Cobalt Catalysts, Some Features of the Catalysts Prepared from Alkyl Aluminum Compounds Containing Al—O—Al Bonds*, by P. Racanelli and L. Porri, published in Europ. Polym. J. 6 751, (1970), pp. 751-761.

*Primary Examiner*—Helen M. S. Sneed
*Attorney, Agent, or Firm*—M. B. Kurtzman

[57] ABSTRACT

A process for the preparation of hydrocarbylalumoxanes comprising oligomeric, linear and/or cyclic hydrocarbylalumoxanes, which comprises contacting a hydrocarbylaluminum dissolved in an inert dry organic liquid with a hydrated salt of a metal which is not reduced during contact with the trihydrocarbylaluminum at temperatures between −30° C. and 110° C.

8 Claims, No Drawings

PROCESS FOR THE PREPARATION OF ALUMOXANES

The present invention relates to the preparation of alumoxanes, preferably methylalumoxanes.

Alumoxanes, i.e. the products of partial hydrolysis of hydrocarbylaluminum compounds, have been found useful in a variety of chemical reactions, among others as catalysts components for polymerization catalysts and especially as a component for catalysts in the preparation of high-activity, homogenous Ziegler catalysts, as is described, for example in U.S. patent application No. 501,740 filed June 6, 1983.

Various processes are known for the preparation of alumoxanes, the simplest being to add water in predetermined amounts and under controlled conditions to an alkylaluminum compound (U.S. Pat. No. 3,242,099). Alumoxanes can also be obtained, for example, by the action of water vapor on a benzene solution of a trialkylaluminum (J. Am. Chem. Soc., 90, 3173 [1968]), by using lithium dialkylaluminates as the organoaluminum starting compound (J. Chem. Soc. 89, 173 [1967]). Other known methods for preparing alumoxanes include oxidizing aluminum-hydrocarbon compounds with lead dioxide (J. Organomet. Chem. 43, 81 [1972]), treating an alkylaluminum with alkyldistannoxanes [($R_3$Sn)$_2$O] in place of water (Racanelli, P. and Porri, L, Europ. Polym. J., 6, 751 [1970]) and hydrolyzing alkylaluminums with copper sulfate containing water of crystallization as suggested in European Patent Application No. 0035242.

In Australian No. 20861/83, Kaminsky et al. disclose a method of preparing alumoxanes by contacting aluminum salts containing water of crystallization with a trialkylaluminum. It is taught that the alumoxanes are obtained in higher yields and greater purity.

In many of these processes, because of the highly exothermic nature of the reaction between the water and the hydrocarbylaluminum, the reaction can easily get out of control or even become explosive. While the use of $CuSO_4.5H_2O$ as a source of water provides for the slow addition of water, thus reducing the risk of local excesses of water and, thereby reducing the probability of a runaway or explosive reaction, the method suffers from some drawbacks; for example, the Cu(II) may be reduced to Cu(I) or even to metallic copper during the reaction with an alkylaluminum such as trimethylaluminum. This can lead to the introduction of sulfate groups and other undesirable types of functionalities as well as copper into the alumoxane preparation. The alumoxane product, therefore, prior to use as a component of a catalyst system in a polymerization process must be filtered, purified and recrystallized, since otherwise adverse conditions will exist during the polymerization and the quality and quantity of the polymer will be adversely affected. Another disadvantage associated with $CuSO_4.5H_2O$ in preparation of alumoxane is the low yield which is in the order of about 30% relative to the aluminum trialkyl employed.

These problems can be essentially eliminated, if one employs hydrated salts as the source of water in the preparation of alumoxanes such as methyl alumoxane wherein the metal component is not reduced during the alumoxane preparation. The metals are selected from the metals of Group 1a, 2a, 2b, 3a and 8b of the Periodic Table (as defined in the Handbook of Chemistry and Physics, 53rd Ed., CRC Press, Cleveland, 1972, P. B-3).

An additional unexpected benefit is the discovery that the catalyst systems comprising the alumoxane prepared through the use of such hydrated salts evidence a much higher activity than catalyst systems comprising alumoxanes prepared from $CuSO_4.5H_2O$, and that this higher activity can be obtained with shorter reaction periods.

The alumoxanes which are prepared in accordance with this invention are oligomeric, linear and/or cyclic hydrocarbylalumoxanes represented by the formulas:

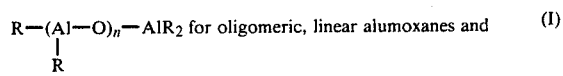

(I)

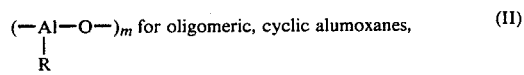

(II)

wherein n is 1–40, preferably 10–20, m is 3–40, preferably 3–20, and R is a $C_1$–$C_8$ alkyl group and preferably methyl. It is generally known that the alumoxanes will show maximum activity when m and n are greater than 10.

In the case of alkylalumoxanes, the general procedure, in accordance with this invention, is to dissolve a trialkylaluminum, preferably trimethylaluminum in an inert aliphatic or aromatic solvent maintained at temperatures between −30° C. and 110° C., preferably between 15° C. and 50° C. and slowly adding the alkylaluminum solution to the hydrated salt. Because the hydrated salts are solids at the contacting temperatures, the salts should be thoroughly mixed with an inert dry organic liquid such as toluene to form a slurry. The liquid to salt ratio should be about 100:1 to 4:1 so as to provide the most useful contacting system. Illustrative of the dry organic liquids one can employ in forming the hydrated salt slurry are toluene, hexane, heptane, octane, cyclohexane and the like.

Because of the very highly exothermic character of the reaction between trialkylaluminum and water, it is important that the reaction not be carried out in too concentrated a system and/or at an excessively high rate. The liquid used to slurry the hydrated salts also serves to dilute the reacting systems as does the inert solvent used for diluting the alkylaluminum compound.

The ratio by volume between the inert solvent and the alkylaluminum employed should be about 1:1 to about 50:1 or greater and preferably about 10:1. The molar ratio of water in the hydrated salt to alkylaluminum should be 0.5:1 to about 1.5:1 and preferably 1:1, calculated on the amount of water in the hydrate salt available for reaction with the organoaluminum compound under the conditions used. This amount will not only depend on the total amount of water present in the hydrated salt, which may not always correspond exactly to the chemical formula given for the compound, but also upon factors which influence the release of water from the salt, such as temperature, time, concentration and degree of communition of the solid.

Completion of the reaction between the trialkylaluminum and the hydrated salt is indicated by the cessation of alkane production. Generally, the reaction time will be between about 0.5 and about 200 hours, and preferably between about 10 and 40 hours, it being controlled primarily by the rate of addition of the trihydrocarbylaluminum to the hydrated salt. However, the rate of addition of the organoaluminum compound that can be advantageously employed is in turn dependent upon a number of factors such as the general tendency of the hydrated salts to give up its water of hydration, the state of subdivision of the salt, the temperature of the reacting system and the concentration of the reactants. The latter two factors are of particular importance also from a safety point of view. Thus, a rapid addition of the trihydrocarbylaluminum at a high concentration of the reactants may lead to an uncontrollably fast reaction. Since the rate at which the water of crystallization is released by the hydrated salts generally increases with the temperature, an increase in temperature may also lead to an uncontrollably fast reaction unless the rate of reaction is limited by other factors such as the rate of addition of the organoaluminum compound to the hydrated salt slurry. For the sake of safety and in order to obtain a product of desirable properties, the rate of trihydrocarbylaluminum addition should not exceed about 1/20th of a mole per minute for each of liter of reaction medium, which in the case of trimethylaluminum would correspond to 3.6 g/min/l. Faster rates should be avoided in order to prevent any possibility of a runaway reaction or explosion. As a rule, with a suitable original hydrated salt slurry concentration corresponding to about 1-10 moles $H_2O$ per liter, the time required for the hydrocarbylaluminum addition would typically be within the range of 20-200 minutes and preferably in the range of 30-100 minutes.

The solvents employed in dissolving the trialkylaluminum can be any of the known inert organic solvents, preferably aliphatic or aromatic solvents such as toluene, benzene, hexane, heptane, isooctane, cyclohexane, methylcyclohexane, decane, and the like, and preferably the same as the solvent employed for slurrying the hydrated salt. The preferred solvents are toluene and hexane.

The hydrocarbylaluminums which are employed as the starting materials in the preparation of the alumoxanes are trialkyl or triarylaluminums represented by the formula $AlR_3$ in which R may be an alkyl group having from 1 to 8 carbon atoms and preferably 1 to 6 carbon atoms or an aryl group having from 6 to 10 carbon atoms. Illustrative of the alkyl groups are methyl, ethyl, propyl, isopropyl, n-butyl, isobutyl, pentyl, hexyl, and the like. Suitable aryl groups are phenyl, benzyl, naphthyl and the like.

The hydrated salts are selected from salts comprising a metal which is not readily reduced by alkylaluminum compounds and which release their water of crystallization reasonably slowly, thus reducing the risk of over-hydrolysis and/or uncontrollably fast reaction. Illustrative of the hydrated salts which can be usefully employed in accordance with this invention are magnesium salt hydrates, zinc salt hydrates, sodium salt hydrates and iron salt hydrates such as $FeSO_4.7H_2O$, $MgSO_4.7H_2O$, $ZnSO_4.7H_2O$, $Na_2SO_4.10H_2O$, $Na_2SO_4.H_2O$, $Na_3PO_4.12H_2O$. Preferably, the salt of choice is $FeSO_4.7H_2O$. Because the water of hydration is not held equally firmly by all of the salt hydrates, some variation of reaction conditions with respect to temperature, concentration of reactants, water/aluminum ratio, etc. will be required for optimum results.

The trialkylaluminum, e.g., trimethylaluminum, diluted in the inert solvent such as heptane or toluene, reacts with the metal salts such as $FeSO_4.7H_2O$ to produce oligomeric, linear and cyclic alumoxanes.

Upon completion of the reaction between the metal salt hydrate and the trialkylaluminum, it is desirable to filter off any solids which may remain and recover the alumoxane solution.

The polyolefins prepared in the presence of the alumoxanes prepared in accordance with this invention can be extruded, mechanically melted, cast or molded as desired. They can be used for plates, sheets, films, and a variety of other objects.

While the invention is described in connection with the specific examples below, it is understood that these are only for illustrative purposes. Many alternatives, modifications and variations will be apparent to those skilled in the art in light of the below examples and such alternatives, modifications and variations fall within the generally scope of the claims.

EXAMPLE 1

A one liter baffled, 3-necked reaction flask was charged inside a nitrogen containing dry box with 55.6 9 ferrous sulfate heptahydrate ($FeSO_4.7H_2O$) and 500 cc dry toluene. A 500 cc feed bottle was likewise charged inside the dry box with 1.4 mole (100.9 g) trimethylaluminum (TMA, $Me_3Al$) diluted to 350 cc with dry toluene. Two adapters, one of which was equipped with a side tube for connection to a nitrogen line, were attached to the side necks of the reaction flask and secured with tension hooks. A bulb from a medicine dropper was placed over the tube for connection to the nitrogen line and double serum stoppers were put over the open ends of the adapters and secured with copper wire. Double serum stoppers were also put over the neck of the feed bottle and secured with copper wire. Finally, a stirrer assembly was put in place and attached to the center neck of the reaction flask with tension hooks.

The flask and the bottle were then transferred to a hood and connected to nitrogen lines, the flask through its side tube and the bottle through a needle stuck through the double serum stopper. The flask was then inserted in a temperature controlled bath, which at this time was set at $-8°$ C., the stirrer attached to the stirrer motor, and the stirring started at 300 rpm. Finally, the bottle and the flask were connected with the help of syringe needles through a piece of tubing that ran through a Masterflex pump.

When the contents of the reaction flask had reached the temperature of the thermostatted bath, the pump was started and TMA solution allowed to flow into the reaction flask at a rate of 2.08 cc/min (0.6 g TMA/min). The pump was stopped after 2 hours, at which time 250 cc solution containing 72.1 g (1 mole) TMA solution had been added to the reaction flask. The reaction mixture was allowed to stir for another hour at $-8°$ C., whereupon the temperature was increased to $0°$ C. After 1 hour at this temperature, the temperature was increased to $10°$ C. and after another hour to $20°$ C., at which temperature the stirred mixture was allowed to remain for 17.5 hours. The reaction flask was then disconnected from the feed line, the stirrer motor, and the nitrogen line and brought into the dry box. The solids in the flask were filtered off with mild vacuum in a fritted glass funnel and washed with four 50 cc portions of dry toluene. The clear colorless alumoxane solution had a volume of 710 cc and was 1.12 molar with respect to aluminum, corresponding to a yield of 79.5%, on the assumption that all TMA had been converted to alumoxane. The alumoxane preparation was tested for polymerization activity as follows.

A one liter stainless steel pressure vessel, equipped with an incline blade stirrer, a septum inlet, a vent line, an external water jacket for temperature control, and inlets for regulated supply of dry ethylene and nitrogen, was dried and deoxygenated with a flow of nitrogen at 80° C. for 30 minutes. Five hundred cc toluene and 3.13 cc (3.5 mmole) of the 1.12 molar alumoxane solution were injected directly into the reaction vessel at room temperature, whereupon the temperature was raised to 80° C. After one minute at this temperature and at a pressure of 0 psig, $3.55 \times 10^{-7}$ mole of bis(cyclopentadienyl)zirconium dichloride ($Cp_2ZrCl_2$) was injected into the reactor as a solution in 1 cc dry toluene. This established a molar Al/Zr ratio of 9860. Ethylene was thereafter introduced continuously for 3 minutes so as to maintain a reactor pressure of 4 atm (gauge). The reaction was terminated by rapidly venting and cooling the reactor to room temperature. The recovered yield of dry high mol. wt. polyethylene was 13.3 g, corresponding to a polymerization rate of $2.05 \times 10^6$ g polymer/g Zr.h.atm.

EXAMPLE 2

An alumoxane preparation was made with the same equipment and according to the same general procedure as in Example 1 except that this time 49.9 g (1/5th mole) of mortared $CuSO_4.5H_2O$ was used in place of the $FeSO_4.7H_2O$ of the preceding example. Also, the reaction time at 20° C. was 18 hours instead of 17.5 hours. The recovered filtered product amounted to 710 ml of alumoxane that was 1.12 molar in Al for a yield of 79.5%, or the same as in the earlier example.

When tested for catalyst activity under the same conditions as in Example 1, the alumoxane of this example produced 7.5 g of high mol. wt. polyethylene in 10 minutes, corresponding to a rate of $0.347 \times 10^6$ g polymer/g Zr.h.atm.

EXAMPLE 3

In the preceding Example 2, the $H_2O$/Al ratio employed in the alumoxane preparation was 1 while the same ratio in Example 1 was 1.4. However, as will be shown by the following two comparative experiments, the optimum ratio for $H_2O$/Al with $CuSO_4.5H_2O$ was found to be about one rather than a higher value. The first experiment was carried out according to the procedure of Example 1 but with $CuSO_4.5H_2O$ as the source of water and with the TMA addition made to the salt slurry at 30° C. and subsequent stirring for another 21 hours at this temperature. The yield was 723 ml of a solution 1.15 molar in Al. When tested under the previously described conditions, the alumoxane produced 11.0 g polyethylene in 4 minutes for a rate of $1.27 \times 10^6$ g polymer/g Zr.h.atm.

The second experiment was carried out with 62.5 g (¼th mole) $CuSO_4.5H_2O$ for a $H_2O$/Al ratio of 1.25. After the reaction mixture had been stirred for 19 hours at 30° C., a yield of 670 ml of a solution 1.11 molar in Al was obtained. When tested under the standard conditions of Example 1, this alumoxane produced 4.5 grams of polyethylene in 5 minutes for a rate of $0.417 \times 10^6$ g polymer/g Zr.h.atm.

This shows that the activity of the alumoxane obtained with $CuSO_4.5H_2O$ does not increase if the $H_2O$/Al ratio is increased substantially above unity. Apparently the water of crystallization is released more readily and more completely from this salt than from $FeSO_4.7H_2O$ under the conditions used in these experiments.

EXAMPLE 4

An alumoxane preparation was made according to the procedure of Example 1, except that the TMA addition to the $FeSO_4.7H_2O$ slurry in toluene was made at 0° C. The mixture was stirred at this temperature for 1 hour and at 10° C. for another hour and then, finally, at 20° C. for 19 hours. The yield was 720 ml of a solution 0.96 molar in Al for a yield of 69.1%. The standard polymerization test was modified relative to the previous examples in that only 2.5 mmoles of alumoxane were used for an Al/Zr ratio of 7000. The yield was 11.7 g polyethylene in 2 minutes for a rate of $2.71 \times 10^6$ g polymer/g Zr.hr.atm.

EXAMPLE 5

An alumoxane preparation was made with $CuSO_4.5H_2O$ as the source of water according to the method described for the first experiment of Example 3, i.e. with TMA added at 30° C. However, in this case the stirring was allowed to continue at this temperature for 69 hours. The yield was 720 ml of a solution 0.922 molar in Al or 66.2% of the TMA employed.

When tested as in Example 4, i.e. at an Al/Zr ratio of 7000, this preparation produced 9.8 g polyethylene in 3 minutes for a rate of $1.51 \times 10^6$ g polymer/g Zr.h.atm.

This shows that the activity of alumoxane preparations made with $CuSO_4.5H_2O$ can be improved by using very long reaction times. However, this increase in activity, which is also associated with a lower alumoxane yield, does not result in a preparation nearly as active as the ones obtainable with $FeSO_4.7H_2O$.

What is claimed is:

1. A process for the preparation of oligomeric, linear and/or cyclic hydrocarbylalumoxane, which comprises reacting at temperatures between $-30°$ C. and 110° C. and a hydrocarbylaluminum dissolved in an inert dry organic liquid with a hydrated salt of a metal selected from $FeSO_4.7H_2O$, $MSO_4.7H_2O$, $ZnSO_4.7H_2O$, $Na_2SO_4.10H_2O$, $Na_3PO_4.12H_2O$.

2. The process in accordance with claim 1 wherein the trihydrocarbylaluminum is trialkylaluminum.

3. The process in accordance with claim 2 wherein the trialkylaluminum is trimethylaluminum.

4. The process in accordance with claim 1 wherein the inert solvent is elected from aliphatic or aromatic solvents.

5. The process in accordance with claim 4 wherein the solvents are selected from toluene, hexane, and heptane.

6. The process in accordance with claim 1 wherein the hydrated salt is $FeSO_4.7H_2O$.

7. The process in accordance with claim 1 wherein the molar ratio between the trihydrocarbylaluminum and the hydrated salt calculated on the amount of water is about 1:0.8 to about 1:2.

8. The process in accordance with claim 6 wherein the motor ratio between the trihydrocarbylaluminum and the hydrated metal salt is 1:1.4.

* * * * *